United States Patent
Weese et al.

(10) Patent No.: US 12,210,586 B2
(45) Date of Patent: Jan. 28, 2025

(54) ASSOCIATING A POPULATION DESCRIPTOR WITH A TRAINED MODEL

(71) Applicant: KONINKLIJKE PHILIPS N.V., Eindhoven (NL)

(72) Inventors: Rolf Jurgen Weese, Norderstedt (DE); Hans-Aloys Wischmann, Henstedt-Ulzburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 571 days.

(21) Appl. No.: 17/422,216

(22) PCT Filed: Jan. 23, 2020

(86) PCT No.: PCT/EP2020/051647
§ 371 (c)(1),
(2) Date: Jul. 12, 2021

(87) PCT Pub. No.: WO2020/156924
PCT Pub. Date: Aug. 6, 2020

(65) Prior Publication Data
US 2022/0083814 A1    Mar. 17, 2022

(30) Foreign Application Priority Data

Jan. 28, 2019  (EP) .................................. 19153977

(51) Int. Cl.
*G06F 18/214* (2023.01)
*G06F 18/21* (2023.01)
(Continued)

(52) U.S. Cl.
CPC ...... *G06F 18/2148* (2023.01); *G06F 18/2193* (2023.01); *G06T 7/11* (2017.01); *G06V 10/422* (2022.01); *G16H 30/40* (2018.01)

(58) Field of Classification Search
CPC .... G06F 18/2148; G06F 18/2193; G06T 7/11; G06V 10/422; G16H 30/40; G06N 3/045;
(Continued)

(56) References Cited

U.S. PATENT DOCUMENTS 7,565,369 B2   7/2009  Fan et al.
9,842,274 B2   12/2017 Rodriguez-Serrano et al.
(Continued)

OTHER PUBLICATIONS

Quintanilha, Igor M. et al. "Detecting Out-Of-Distribution Samples Using Low-Order Deep Features Statistics." (2018); (Year: 2018).*
(Continued)

*Primary Examiner* — Ping Y Hsieh
*Assistant Examiner* — Vaisali Rao Koppolu
(74) *Attorney, Agent, or Firm* — Sherry Austin

(57) ABSTRACT

A model may be trained on a training dataset, e.g., for medical image processing or medical signal processing tasks. Systems and computer-implemented methods are provided for associating a population descriptor with the trained model and using the population descriptor to determine whether records to which the model is to be applied, conform to the population descriptor. The population descriptor characterizes a distribution of the one or more characteristic features over the training dataset, with the characteristic features characterizing the training record and/or a model output provided when the trained model is applied to the training record. For instance, the model may be applied only to records conforming to population descriptor, or model outputs of applying the model to non-conforming records may be flagged as possibly untrustworthy.

20 Claims, 4 Drawing Sheets

(51) Int. Cl.
*G06T 7/11* (2017.01)
*G06V 10/422* (2022.01)
*G16H 30/40* (2018.01)

(58) Field of Classification Search
CPC .......... G06N 5/01; G06N 20/20; G06N 20/10; G06N 3/084
See application file for complete search history.

(56) References Cited

U.S. PATENT DOCUMENTS

| | | | | |
|---|---|---|---|---|
| 10,325,224 | B1* | 6/2019 | Erenrich | G06N 5/04 |
| 2006/0184475 | A1* | 8/2006 | Krishnan | G16H 50/20 |
| | | | | 706/20 |
| 2016/0189000 | A1* | 6/2016 | Dube | G06F 18/22 |
| | | | | 382/160 |
| 2016/0364538 | A1* | 12/2016 | Das | G16H 50/70 |

OTHER PUBLICATIONS

Saalbach, Axel, et al. ("Failure analysis for model-based organ segmentation using outlier detection." Medical Imaging 2014: Image Processing. vol. 9034. SPIE, 2014; (Year: 2014).*

Brosch et al: "Foveal Fully Convolutional Nets for Multi-Organ Segmentation"; Medical Imaging 2018, Image Processing, Proceedings of SPIE, vol. 10574, pp. 105740U-1-105740U-9.

Ecobert et al: "Segmetnation of the Heart and Great Vessels I CT Images Using a Model-Based Adaptation Framework"; Medical Image Analysis 15(2011), pp. 863-876.

Hendrycks et al: "A Baseline for Detecting Misclassified and Out-Of-Distribution Examples in Neural Networks"; arXiv:1610.02136V3, Oct. 3, 2018 , 12 Page Article.

Hodge et al: "A Survey of Outlier Detection Methodologies"; Artifical Intelligence Review 22, pp. 85-126, 2005.

PCT/EP2020/051647 ISR & Written Opinion, Apr. 24, 2020, 20 Page Document.

Mitchell: "Study Team Tricks AI Programs Into Misclassigying Diagnostic Images"; Health Care Business News, Jun. 11, 2018.

Niethammer et al: "Global Medical Shape Analysis Using the Laplace-Beltrami Spectrum"; Med Image Comput Comput Assist Inter, 2007; 10(PT.1), pp. 850-857.

Porter: "Testing Consistency of Two Histograms"; arXiv:0804.0380v1, Apr. 2, 2008, pp. 1-35.

Quintanilha et al: "Detecting Out-Of-Distribution Samples Using Low-Order Deep Feature Statistics"; Dec. 21, 2018, Retrieved From The Internet:https://openreview.net/pdf?id=rkgpCoRctm, on Jul. 8, 2019.

Raza et al: "Learning With Covariate Shift-Detection and Adaptation in Non-Stationary Environments:Application to Brain-Computer Interface"; IEEE 2015, 8 Page Article.

Saalbach et al: "Failure Analysis for Model-Based Organ Segmentation Using Outlier Detection"; Medical Imaging 2014:Image Processing, Proceedings of SPIE, vol. 9034, 2014, pp. 903408-1-903408-7.

Vercauteren et al: "Non-Parametric Diffeomorphic Image Registration With the Demons Algorithm"; MICCAI 2007, Part II, LNCS 4792, pp. 319-326, 2007.

"Spectral Shape Analysis", Wikipedia, Originally Downloaded From: https://en.wikipedia.org/wiki/Spectral_shape_analysis, Jun. 2018.

* cited by examiner

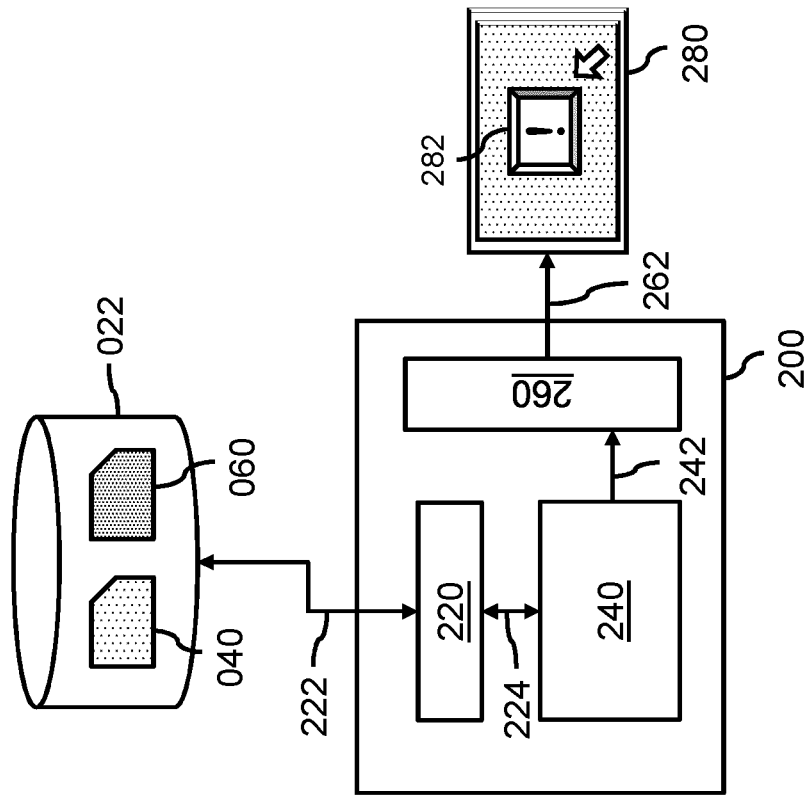
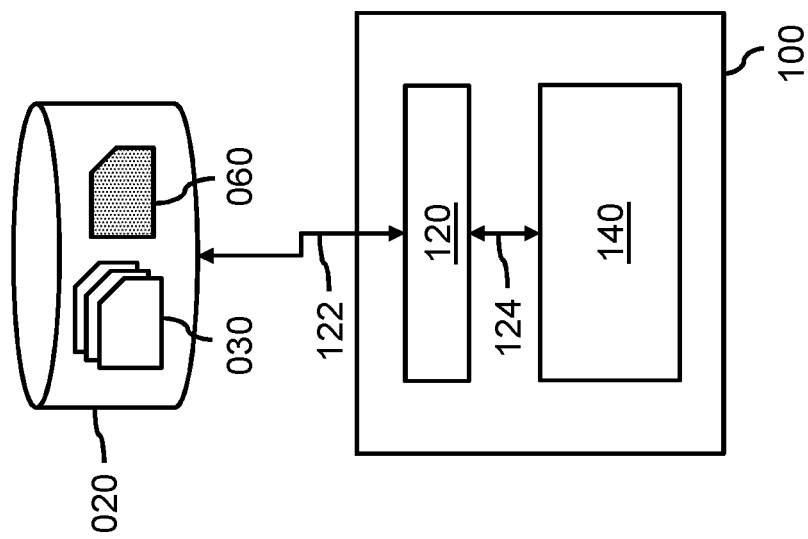

ASSOCIATING A POPULATION DESCRIPTOR WITH A TRAINED MODEL

CROSS-REFERENCE TO PRIOR APPLICATIONS

This application is the U.S. National Phase application under 35 U.S.C. § 371 of International Application No. PCT/EP2020/051647, filed on Jan. 23, 2020, which claims the benefit of European Patent Application No. 19153977.4, filed on Jan. 28, 2019. These applications are hereby incorporated by reference herein.

FIELD OF THE INVENTION

The invention relates to a system for processing training records of a training dataset, e.g., medical records or images. The invention further relates to a system for processing at least one record on which a trained model is to be applied. The invention further relates to a method of processing training records and a method of processing at least one record. The invention further relates to a computer-readable medium comprising instructions to perform either computer-implemented method or comprising a trained model.

BACKGROUND OF THE INVENTION

For many tasks in (medical) image processing and (medical) signal processing, hard-coded and/or statically configured representations of knowledge are being replaced by solutions created using Artificial Intelligence (AI), such as Machine-Learning (ML) and/or Deep Learning (DL) methods. For instance, one particularly relevant area for applying machine learning is automatic (medical) image segmentation. In practice, performing image segmentation in a fully automated way has turned out to be challenging, and in particular, it is difficult to produce the accuracy required for various clinical applications such as radiotherapy planning, pre-operative planning, and the like.

Various ML/DL tools may be used to automatically determine patterns and correlations underlying a training dataset, for instance, supervised learning approaches wherein a (large) training data set is annotated with ground truth. Created models are typically executed at run-time on previously unseen data, usually in an execution environment that is disconnected from the training data. For instance, one reason for disconnecting the execution environment from the training data may be to prevent unnecessary storage of the training data in the execution environment; indeed, storage and processing requirements can be orders of magnitude bigger for the learning phase than for the execution phase. Another reason may be that the training datasets can have requirements arising from legal provisions and/or contractual agreements on Data Ownership, Confidentiality, Privacy, Consent, Data Residency/Geography, or any Data Usage Agreements that prohibit or limit its disclosure or distribution.

The accuracy of an output of applying a model to an unseen record may depend greatly on the training dataset that the model has been trained on. For instance, a model output may be expected to be accurate if the record to which the trained model is applied is sufficiently close or similar to prevalent cases in the training dataset, while the result may be less accurate, or at least there may be more uncertainty about its accuracy, if the record is less close to the training dataset. For example, the record to which the model is to be applied may represent an unusual case or a rare condition in the training dataset. Potential inaccuracies of model outputs may be particularly relevant in pipelines that are expected to work fully automatically without supervision, for instance, image analysis pipelines. However, also for interactive applications, it is important to deal with the possibility of inaccurate model outputs.

SUMMARY OF THE INVENTION

It may be desirable to deal with trained models providing possibly inaccurate model outputs, for instance, in cases where the model is to be applied to records that are substantially different, e.g., relatively far away, from the records of the training dataset that the model was trained on. For instance, it may be beneficial to detect and/or flag application of a model on records for which reduced accuracy may be expected, for example, records that do not conform to a population of the training dataset in terms of model inputs and/or outputs. For instance, being able to detect and/or flag such cases may help to use model outputs in an automated way, but also to warn users in an interactive application that a model output may be inaccurate, for example, to avoid reducing trust in the system by displaying inaccurate results without warning.

The following aspects of the invention may involve determining a population descriptor associated with a trained model. The population descriptor may characterize a distribution of one or more characteristic features of training records of the training dataset that was used to train the trained model. The characteristic features of a training record may characterize the training record, a model output of applying the trained model to the record, or both. The population descriptor may be used to determine deviations of the one or more characteristic features over the training dataset, e.g., in order to determine whether records conform to the population descriptor. For example, model outputs of applying the model to conformant records may be trusted more than model outputs of applying the model to non-conformant records. In case of non-conformance, an output signal may be generated, e.g., to warn the user.

In accordance with a first aspect of the invention, a system is provided for processing training records of a training dataset. This system comprises:

a data interface for accessing:
    a training dataset for a trained model, the training dataset comprising a plurality of training records, wherein the trained model is trained on the training dataset to provide a model output when applied to a record;

a processor subsystem configured to:
    determine one or more characteristic features for a training record of the training dataset, said one or more characteristic features characterizing the training record and/or a model output provided when the trained model is applied to the training record, said characteristic features being based on the training record and/or metadata associated with the training record and/or the model output;
    determine a population descriptor characterizing a distribution of the one or more characteristic features over the training dataset, wherein said determining does not access intermediate outputs of the trained model;
    associate the population descriptor with the trained model to enable an entity which applies the trained model to at least one record to determine whether the at least one record conforms to the population descriptor by determining the one or more characteristic features for the at least one record and by determining a deviation of said one or more characteristic features from the distribution of said characteristic features over the training dataset.

In accordance with a further aspect of the invention, a system is provided for processing at least one record to which a trained model is to be applied. This system comprises:
a data interface for accessing:
a population descriptor associated with the trained model, the trained model having been trained on a training dataset, the training dataset comprising a plurality of training records, the population descriptor characterizing a distribution of one or more characteristic features for the training records over the training dataset, the one or more characteristic features of a training record characterizing the training record and/or a model output provided when applying the trained model to the training record, the one or more characteristic features being determined based on the at least one record and/or metadata associated with the at least one record and/or a model output of the trained model for the at least one record, the population descriptor having been determined based on the characteristic features without accessing intermediate outputs of the trained model;
the at least one record to which the trained model is to be applied;
a processor subsystem configured to:
determine the one or more characteristic features of the at least one record;
determine a deviation of the one or more characteristic features of the at least one record from the distribution of said characteristic features over the training dataset to determine whether the at least one record conforms to the population descriptor;
if the at least one record does not conform to the population descriptor of the trained model, generate an output signal indicative of said non-conformance.

In accordance with a further aspect of the invention, a computer-implemented method is provided of processing training records of a training dataset. This method comprises:
accessing:
a training dataset for a trained model, the training dataset comprising a plurality of training records, wherein the trained model is trained on the training dataset to provide a model output when applied to a record;
determining one or more characteristic features for a training record of the training dataset, said one or more characteristic features characterizing the training record and/or a model output provided when the trained model is applied to the training record, said characteristic features being determined based on the training record and/or metadata associated with the training record and/or the model output;
determining a population descriptor characterizing a distribution of the one or more characteristic features over the training dataset, wherein said determining does not access intermediate outputs of the trained model;
associating the population descriptor with the trained model to enable an entity which applies the trained model to at least one record to determine whether the at least one record conforms to the population descriptor by determining the one or more characteristic features for the at least one record and by determining a deviation of said one or more characteristic features from the distribution of said characteristic features over the training dataset.

In accordance with a further aspect of the invention, a computer-implemented method is provided of processing at least one record to which a trained model is to be applied. This method comprises:
accessing:
a population descriptor associated with the trained model, the trained model having been trained on a training dataset, the training dataset comprising a plurality of training records, the population descriptor characterizing a distribution of one or more characteristic features for the training records over the training dataset, the one or more characteristic features of a training record characterizing the training record and/or a model output provided when applying the trained model to the training record, the one or more characteristic features being determined based on the at least one record and/or metadata associated with the at least one record and/or a model output of the trained model for the at least one record, the population descriptor having been determined based on the characteristic features without accessing intermediate outputs of the trained model;
the at least one record to which the trained model is to be applied;
determining the one or more characteristic features of the at least one record;
determining whether the at least one record conforms to the population descriptor by determining a likelihood of the one or more characteristic features of the at least one record occurring according to their distribution over the training dataset;
if the at least one record does not conform to the population descriptor of the trained model, generating an output signal indicative of said non-conformance.

In accordance with a further aspect of the invention, a computer-readable medium is provided comprising transitory or non-transitory data representing instructions arranged to cause a processor system to perform either or both computer-implemented methods.

In accordance with a further aspect of the invention, a computer-readable medium is provided comprising transitory or non-transitory data representing a trained model and a population descriptor associated with the trained model, the trained model having been trained on a training dataset, the training dataset comprising a plurality of training records, the population descriptor characterizing a distribution of one or more characteristic features for the training records over the training dataset, the one or more characteristic features of a training record characterizing the training record and/or a model output provided when applying the trained model to the training record, the one or more characteristic features being determined based on the at least one record and/or metadata associated with the at least one record and/or a model output of the trained model for the at least one record, the population descriptor having been determined based on the characteristic features without accessing intermediate outputs of the trained model.

The above measures involve a trained model that is trained on a training dataset. The training dataset, which is sometimes also called training data, may comprise a plurality of training records, which are sometimes also called training examples. The described techniques are applicable to a wide range of training datasets, for example, comprising medical images, patient records, or non-medical data such as measurements of the performance of a machine that is to be optimized, financial information, etcetera.

The trained model may be trained to provide a model output when applied to a record. Any suitable type of model output known from machine learning may be combined with the described techniques, for example, classifications, regressions, clusterings, etcetera. Many such suitable machine learning models are known in the art. Various techniques for training a model are known in the art per se and may be used. The training may be supervised or semi-supervised, e.g., some or all of the training records may comprise an input object and a desired output value. The training may also be unsupervised. When using a model output of a training record for supervised learning, the desired output value and/or the output of applying the trained model to the training record may be used.

The above features also involve one or more characteristic features of a training record being determined. The characteristic features may characterize the training record, a model output of applying the trained model to the training record, or both. For example, a characteristic feature may correspond to, or be based on, a feature of the training record, e.g., an intrinsic feature, a derived feature, or metadata, and/or a feature of the result of applying the trained model to the record. The characteristic features may be key features of the training record or model output that, when determined for all training records or at least a substantive part of the training records of the training dataset, are known or expected to be descriptive of the population of the training dataset. For example, the characteristic features may be features of the training record which were used as input to the training of the model, but also metadata that was not necessarily used to train the model, or model outputs of applying the model. Generally, the characteristic features may be preselected, e.g., by a user. However, it is possible instead or in addition to make an automated selection of characteristic features, e.g., based on a principal component analysis of potential features. A record may have one characteristic feature, but in other embodiments, a record has multiple characteristic features, e.g., at least or at most 3, 5, or 10.

The above features also relate to a population descriptor. The population descriptor may characterize a distribution of the one or more characteristic features over the training dataset. Typically, the population descriptor is determined based on the characteristic features associated with the training records. Thereby, given a record, e.g., a non-training record, the population descriptor may allow to determine a deviation of the one or more characteristic features of a record from the distribution of these characteristic features over the training dataset, e.g., to determine whether the record conforms to the population descriptor. For example, based on the characteristic features, it may be possible to determine whether or not the record is an outlier, e.g., whether the record would be unlikely to occur, of have occurred, in the training population or in a population from which the training dataset was drawn.

Conformance of a record to the population descriptor may indicate that the record is in some sense a normal record, e.g., a record inside the scope of the training set. If this is the case, it may be determined that the model output resulting from applying the trained model is trustworthy. For example, the record may be from a population that is well-represented in the training set, the model output may be of a type that is well-represented in the training set, or both. In such cases, the model output may be expected to be accurate. If the record is determined not to conform to the population descriptor, this may indicate that the record is out of scope for the trained model, e.g., the model output of applying the trained model may be expected to be less trustworthy. For example, the record may be from a population that is underrepresented in the training set and/or the model output is of a type that is underrepresented in the training set.

As an example, a neural network trained to segment a normal heart in magnetic resonance (MR) images may not work satisfactorily when applied to a severe congenital heart disease case with transposition of the great arteries, e.g., this rare condition may not be represented in the training dataset. In effect, conformance or non-conformance to the population descriptor may indicate that a record is in-spec or out-of-spec for the trained model, e.g., conceptually, the record lies inside or outside of a convex hull defined by the training set.

The inventors have found that a population descriptor as described above may be particularly suitable for determining conformance of records. Since the population descriptor is based on characteristic features characterizing the training record and/or model outputs, it is applicable to a wide range of machine learning models and, can, to a large extent, be agnostic of the particular machine learning model used to train the model. Moreover, the population descriptor is generally limited in size compared to the training dataset and/or the trained model, so that associating the population descriptor with the training dataset may incur relatively little overhead in terms of storage and processing, especially when compared to storing the training dataset for determining conformance. Moreover, since a population descriptor typically comprises aggregated data, using a population descriptor for conformance may circumvent various ownership, confidentiality, privacy, consent, and/or residency/geography restrictions involved in storing the training dataset for determining conformance.

The population descriptor may be associated with the trained model to enable an entity applying the trained model to at least one record to determine whether the at least one record conforms to the population descriptor. For example, the population descriptor may be encoded as metadata associated with the trained model, in any suitable manner, e.g., by including the population descriptor in the trained model itself, e.g., as a file header, XML element, etc., or by providing the population descriptor as a separate file, or in any other manner.

During the processing of at least one record to which the trained model is to be applied, the population descriptor may be used to determine a deviation of the one or more characteristic features of the at least one record from the distribution of said characteristic features over the training dataset. For this, the one or more characteristic features of the at least one record may first be determined, e.g., the one or more characteristic features may be determined for each record the trained model is to be applied to. For characteristic features characterizing model outputs, determining the characteristic features may comprise applying the trained model to the at least one record to obtain at least one model output, e.g., a model output for each record the trained model is to be applied to. By determining the deviation, it may be determined whether the at least one record conforms to the population descriptor associated to the trained model. The deviation may comprise a deviation value, e.g., a continuous value that can be compared to a threshold and/or a deviation decision, e.g., a binary decision of deviation or non-deviation.

Determining conformance may comprise performing one or more conformance checks, each check being with respect to a respective subset of characteristic features, e.g., one, multiple, or all characteristic features. For instance, conformance may be determined separately with respect to each characteristic feature that was used to determine the population descriptor, or jointly with respect to all characteristic features that were used to determine the population descriptor. However, this is not necessary, e.g., conformance may also be determined with respect to a subset of the characteristic features that were used to determine the population descriptor.

Based on the determined characteristic features, a deviation of the one or more characteristic features of the at least one record from the distribution of these characteristic features over the training dataset may be determined. Hence, it may be determined whether the at least one record conforms to the population descriptor. If the record does not conform to the population descriptor, an output signal may be generated indicative of the non-conformance.

In various embodiments, conformance may be determined for a single record. This may indicate whether the model output of applying the trained model to that specific record is expected to be trustworthy, accurate, in-spec, etc., as also discussed above. The output signal may be used, for instance, to warn the user, to refrain from using the model output provided by the trained model, etcetera. Determining conformance by a population descriptor may avoid to needlessly restrict application of the model. For example, explicit/manual coding of a particular age bracket, ethnicity, geography, etc., on which the model was trained may be avoided. As a consequence, the trained model may be used beyond the training cohort and geography according to the population descriptor, allowing application to additional subjects that are still in the scope of the model.

In various embodiments, conformance may be determined for a group of multiple records, providing an assessment of the conformance of the multiple records, as a group, to the population descriptor. This may indicate whether the group of records, e.g., a cohort of patients, is representative of the training set. For example, this may allow to detect model/concept drift. Interestingly, this way, model/concept drift may be detectable without requiring an explicit coding of conditions under which the model may be applied, e.g., geographies of which patients were included in the training set. Moreover, it may be prevented that application of the trained model is needlessly limited to the particular setting of the training set, e.g., its geography. Indeed, the model may be applicable more widely than the training set, the population descriptor allowing to detect that the records the model are applied on are no longer sufficiently conformant to the training set. The output signal can again be used to warn the user.

Optionally, the output signal can be used to adapt a model parameter of the trained model. For example, the model parameter may be adapted to adapt the model to a change in the type of record the model is applied to compared to the training dataset, as indicated by the signal. For example, one or more model parameters may be increased or decreased or one or more model flags may be set or reset, e.g., a model parameter may be adapted to increase sensitivity of the model at the expense of specificity or the other way around. As a concrete example, non-conformance of several records individually or as a group, e.g., model/concept drift, may indicate a higher-than-usual incidence of diagnoses of a particular disease and hence suggest an outbreak of the disease, at which point it may be useful to temporarily increase the sensitivity of the model in order to assist in proactively combatting the outbreak, even if this could result in a lower specificity. In an embodiment, the model parameter is adapted to output signals accumulated over multiple records to which the trained model is applied, e.g., a set or cohort of unseen records. For example, model parameters may be tuned periodically, e.g., every week, every four weeks, etc.

Optionally, the trained model is neural network, for example, a deep neural network or a convolutional neural network (CNN). Such a neural network may be trained using training methods that are known per se, for instance, using backsubstitution and/or stochastic gradient descent. However, other known types of models and training methods are equally applicable, e.g., decision trees, for instance, trained using ID3 or C4.5; support vector machines (SVMs); random forests; k-means clustering; or autoencoders.

Optionally, the population descriptor is encoded, e.g., for associating with the trained model, wherein the encoding of the population descriptor may comprise feature identifiers of the one or more characteristic features. Any feature identifier suitable for indicating to an entity using the trained model how to compute a characteristic feature of a record may be used, e.g., an index or a name of feature of the record or model output, an identification of function for computing the characteristic feature, e.g. "num_pixels_darker_than(100)" or "<feature value 1>+<feature value 2>+<model output 1>", or executable code for computing the characteristic feature from the record, associated metadata, and/or the model output of applying the trained model to the record. Including feature identifiers may have as an advantage that it allows processing of records with reduced configuration and/or improved flexibility.

Optionally, the population descriptor may comprise probability data indicative of probability distribution of one or more characteristic features over the training dataset. The probability data may be used to determine a probability of the determined characteristic features occurring according to the probability data. For example, the probability data may allow to determine an estimate of the likelihood of the set of characteristic features occurring in the training population from which the training dataset was sampled.

Optionally, the probability data may comprise parameters of a probability distribution of one or more characteristic features. The parameters may be the parameters of a given probability distribution, e.g., normal or Gaussian, that best match the training dataset. For example, the probability data may comprise parameters of a univariate probability distribution of at least one characteristic feature, for example, a mean and standard deviation of a normal distribution, a rate of an exponential distribution, etcetera.

Optionally, the probability data comprises one or more quantiles of a characteristic feature, e.g., a median, or one or more tertiles, quartiles, percentiles, etcetera. For instance, the probability data may comprise each percentile of a characteristic feature, e.g., a characteristic feature expressed as a continuous variable. For example, for continuous variables that do not follow a Gaussian distribution, using quantiles may be particularly advantageous in terms of space and/or computational requirements and/or in terms of their robustness, e.g., insensitivity to outliers, skew, etc.

Optionally, the probability data comprises a histogram of one or more characteristic features. For example, the histogram may comprise occurrence counts of values or value ranges over the training dataset for the at least one characteristic feature.

Optionally, the probability data comprises data indicative of a joint probability distribution of multiple characteristic features. This may allow to determine a probability, e.g., joint probability, of the multiple characteristic features of the record occurring according to this probability data. For instance, the probability data may comprise parameters of a multivariate probability distribution of multiple characteristic features, a histogram of occurrences of combinations of the multiple characteristic features, etcetera.

When processing at least one record to which the trained model is to be applied, the probability data and characteristic features determined for a record may be used to determine a probability of the determined characteristic features occurring according to the probability data. The probability may, for instance, be an absolute probability of the determined characteristic features occurring according to the probability data. The probability may also be a relative probability, e.g., a probability that a present value for a particular characteristic feature or set of characteristic occurs as compared to the most common value of the feature or set of features. The probability may also be a probability of a higher, of a lower value, or of a less common value than the present value occurring in the training set for a characteristic feature or set of characteristic features. Generally, the use of probabilities may allow to provide a robust and detailed assessment of conformance to the population descriptor. Moreover, the use of probabilities may allow to provide explainable feedback allowing a user to understand on what basis a conformance decision was made.

Optionally, the population descriptor may comprise a correlation value indicative of a correlation between two characteristic features. The correlation value may for instance indicate that two characteristic features are likely to have relatively high values at the same time or that one characteristic feature usually has a high value when another characteristic feature has a low value. For instance, the correlation value may be a Pearson or Spearman correlation, or similar. The correlation value may also be a covariance measure between the characteristic features. For instance, the population descriptor may comprise a covariance matrix providing covariances between multiple respective first and second characteristic features. Using probabilities of multiple characteristic features may improve the accuracy of conformance decisions by allowing to take into account co-occurrence of characteristic features with each other, e.g., if a low value of one characteristic feature is seldom combined with a high value of another characteristic feature in the training dataset, then such a combination of feature values may indicate non-conformance. However, probability estimates for multiple characteristic features may also be determined based on data indicative of the probability distribution of the individual characteristic features, e.g., by assuming that the characteristic features are statistically independent/uncorrelated.

Optionally, the probability data comprises data may comprise data indicating a temporal variability of one or more characteristic features over the training dataset. For example, the training dataset may comprise time-series data. The temporal variability data may comprise, for instance, median and temporal variance references, for example, for the positivity rate of a model output. For example, the data from the training dataset may be time-boxed in one-day, one-week, or one-month boxes. For example, during use, conformance of multiple records to the temporal variability data may be determined, e.g., based on determining a significant deviation of the actual positivity rate. In such cases, an output signal, e.g., a model drift alert, may be generated and possibly output to a user, e.g., a clinical user or a data science expert.

The probability data may comprise separate probability data for multiple characteristic features or for, possibly overlapping, sets of multiple characteristic features. Hence, the probability data may enable conformance checking with respect to multiple features or sets of features. To check conformance, a determined probability may be compared to a predefined threshold to check conformance, for example, non-conformance may be determined if the probability is below the threshold. Multiple probabilities may also be determined, e.g., each of them may be compared to a threshold and non-conformance may be determined if a predefined number of values meet the threshold, the probabilities may be multiplied and the result compared to the threshold, etcetera.

Optionally, the population descriptor may comprise a one-class classifier. As is known in the art per se, a one-class classifier, also known as a unary classifier or a class-modeler, may be constructed to identify objects of a certain class amongst a larger set of objects. Such a one-class classifier is typically primarily trained on objects of that class. The one-class classifier may be used to classify the at least one record as being conformant, and may be trained on the sets of characteristic features of the training records. This may enable to make conformance decisions using relatively complex decision boundaries and/or enable improved automation of performing conformance checks, e.g., the classifier may be periodically re-trained. Various one-class classifiers known from the literature may be used. Optionally, the one-class classifier comprises a one-class support vector machine (SVM).

Optionally, a training record may comprise an image. For example, the image may be a medical image, e.g., obtained from a CT or MRI scanner. The processor subsystem may be configured to determine the one or more characteristic features of the training record my extracting a characteristic feature from the image, e.g., from the actual image data, e.g., pixels of the image. For example, a characteristic feature may be a feature, e.g., statistic, of the overall image, such as an average greyscale value, or a feature of a particular part of the image or of a particular object recognized in the image. The processor subsystem may also be configured to determine a characteristic feature from metadata associated with the image. For example, the metadata may be any data apart from the image data, e.g., apart from the pixels of the image. For example, the metadata may describe imaging conditions, e.g., image size, focal length, date, time, etc., and/or an entity on the image, e.g., patient data of an imaged patient. A specific example of such metadata is DICOM (Digital Imaging and Communications in Medicine) metadata.

Optionally, the trained model may be trained to provide a segmentation of the image. For example, such a segmentation may partition the image into multiple segments of pixels. An image segment can represent, for instance, an imaged object or a contour, e.g., a 2D contour, or surface, e.g., a 3D surface, of an imaged object. The processor subsystem may be configured to determine a characteristic feature of the training record by extracting a shape descriptor of the segmentation of the image. For example, a shape descriptor may be a simplified representation of a shape recognized in the image, e.g., a congruency-invariant shape descriptor, an intrinsic shape descriptor, etcetera. Optionally, a characteristic feature is a property of a recognized shape, e.g., determined from the respective shape descriptor, e.g., an area, a volume, an orientation, a location, etcetera.

Optionally, during the training of the training dataset, weights may be assigned to records of the training dataset. In such cases, the population descriptor may be determined according to these assigned weights. For instance, during the training of the training dataset, the training dataset may be rebalanced, for example, in order to reduce an imbalance between the number of training records of various classes. For instance, such rebalancing may comprise duplicating records of the training dataset for use during the training. These weights may be taken into account in the population descriptor, for instance, when building a histogram, a record that has been duplicated during the training may be added to the histogram with a weight corresponding to the number of times it has been duplicated. For example, the population descriptor may be determined based on the rebalanced training dataset.

Optionally, the system that determines the population descriptor may also train a machine learning model on the training dataset, thereby obtaining the trained model. Since both the training and the determining of the population descriptor typically access the training dataset, this may have as an advantage that less duplication/sharing of the training dataset is needed. Interestingly, however, the determination of the population descriptor typically does not need to access internals of the training of the machine learning model, e.g., intermediate outputs of the machine learning model, and hence, the module for determining the population descriptor can be arranged relatively independently from the training of the model.

Optionally, the system processing the at least one record is further configured to apply the trained model to the at least one record to obtain at least one model output. In some embodiments, the system applies the trained model to the at least one record only if no non-conformance signal is generated. In other embodiments, the system applies the trained model even in case of a non-conformance signal, e.g., the system provides the at least one model output along with an indication of conformance or non-conformance. The model output may also be used to determine the one or more characteristic features, e.g., characteristic features characterizing model outputs.

Optionally, the system processing the at least one record further comprises an output interface for outputting an output signal that indicates non-conformance of at least one record. The output signal may be output to a rendering device for rendering the output signal in a sensory perceptible manner. To output the signal, the rendering device may comprise a screen on which the output signal is displayed, e.g., in the form of a pop-up box, a highlighting of the at least one record in a list of records, a coloring of the respective model output, etcetera. Other types of rendering devices may be used instead or in addition, e.g., a speaker playing a warning sound, etcetera.

Through the rendering of the output signal, the user may obtain feedback that the at least one record does not conform to the population descriptor. For instance, the output signal may be rendered alongside a rendering of at least one model output of applying the trained model to the at least one record. In some embodiments, e.g., when a user has requested the model to be applied to a record, the model output may be rendered along with the determined conformance or non-conformance. In other embodiments, if non-conformance is determined, the model output may be suppressed, or may not be determined at all. In yet other embodiments, model outputs may be shown only of non-conformant records, e.g., records of which conformance is determined are processed automatically and non-conformant records are presented for review by a user. Accordingly, the user can be alerted in various ways to the fact that some model outputs may be less trustworthy.

Optionally, a deviation of one or more determined characteristic features that resulted in non-conformance to the population descriptor may be output in a sensory perceptible manner to a user. This may enable the user to obtain insight as to why non-conformance was determined. For instance, it may be reported that, on the basis of a combination of a particular set of characteristic features, non-conformance was determined.

Optionally, a degree of deviation is reported, for instance, the deviation may comprise a probability of the one or more characteristic features occurring according to probability data of the population descriptor. For instance, a probability of a record having more extreme values for the characteristic features than the present record may be reported, e.g., a warning may be given that "in the training set, only 1% of patients were female and taller than the present patient" or "the training set does not include a lung that big for a baby that young". Many variations will be apparent.

Optionally, population descriptors associated to multiple trained models are accessed by the data interface of the system using the trained model. The multiple trained models may differ, for instance, in the training dataset on which they were trained, and/or in the type of model, e.g., an SVM or a neural network, and/or in the parameters used to train the model. The processor subsystem of the system may be configured to determine whether the at least one record conforms to a population descriptor associated with a respective trained model, and, in case of conformance, select the respective trained model of the multiple trained models. For instance, the processor subsystem may determine, for each trained model, whether the at least one record conforms to its model population descriptor, thus obtaining a set of conformant trained models. The respective trained model may be selected from the set of conformant trained models. The selected trained model may be used, e.g., to determine an overall model output for a record as a model output of applying the selected trained model to the record. Multiple trained models may be selected. For instance, an overall model output may be determined from model outputs of applying the multiple selected trained models to the record, e.g., by majority vote, averaging, etc. of the model outputs. This way, a model output with overall increased accuracy may be obtained since the most appropriate model or models for the record are used. It is also possible to present model outputs of multiple trained models, for example, with the selected trained model or trained models highlighted, allowing a user to make a more informed decision on which model output to use.

The selection of the trained model may be based on the conformance/non-conformance determination. The selection of the trained model may also be based on intermediate results leading to the conformance/non-conformance determination, e.g., determined probabilities of the one or more characteristic features of the record occurring according to respective probability data, confidence values of respective one-class classifiers in classifying a record as being conformant, etcetera. For instance, the model with the highest probability, confidence, etc., may be selected. The model outputs may be presented to the user along with the respective probability, confidence, etc.

Generally, a trained model maybe selected based on conformance of characteristic features characterizing the training record, based on conformance of characteristic features characterizing a model output of applying the trained model to the training record, or based on both in a hybrid approach. For instance, the first possibility may allow to select a trained model a priori based on the best matching input data representation among multiple training datasets, e.g., trained using the same kind of model and/or model parameters. The second possibility may allow to select a trained model a posteriori based on a highest likelihood of the model output among model outputs of the respective models. This second possibility may for instance be used when multiple different models were trained on the same dataset.

Optionally, determining the conformance is further based on determining whether the one or more characteristic features satisfy one or more predefined domain constraints. This may enable various kinds of domain knowledge to be integrated in the determination, increasing its overall accuracy. For instance, a domain constraint may comprise a range of possible values of a characteristic parameter, e.g., an age is between 0 and 130, a weight is positive, etcetera.

It will be appreciated by those skilled in the art that two or more of the above-mentioned embodiments, implementations, and/or optional aspects of the invention may be combined in any way deemed useful.

Modifications and variations of a system for processing training records of a training dataset or a system for processing at least one record to which a trained model is to be applied, can be carried out by a person skilled in the art on the basis of the present description. Modifications and variations of any computer-implemented method and/or any computer program product, which correspond to the described modifications and variations of a corresponding system, can be carried out by a person skilled in the art on the basis of the present description.

BRIEF DESCRIPTION OF THE DRAWINGS

These and other aspects of the invention will be apparent from and elucidated further with reference to the embodiments described by way of example in the following description and with reference to the accompanying drawings, in which FIG. 1 shows a system for processing training records of a training dataset to determine a population descriptor that characterizes a distribution of one or more characteristic features over the training dataset;

FIG. 2 shows a system for processing at least one record on which the trained model is to be applied, and determining whether the at least one record conforms to the population descriptor;

It should be noted that the figures are purely diagrammatic and not drawn to scale. In the figures, elements which correspond to elements already described may have the same reference numerals.

LIST OF REFERENCE NUMBERS

Figure 3B:
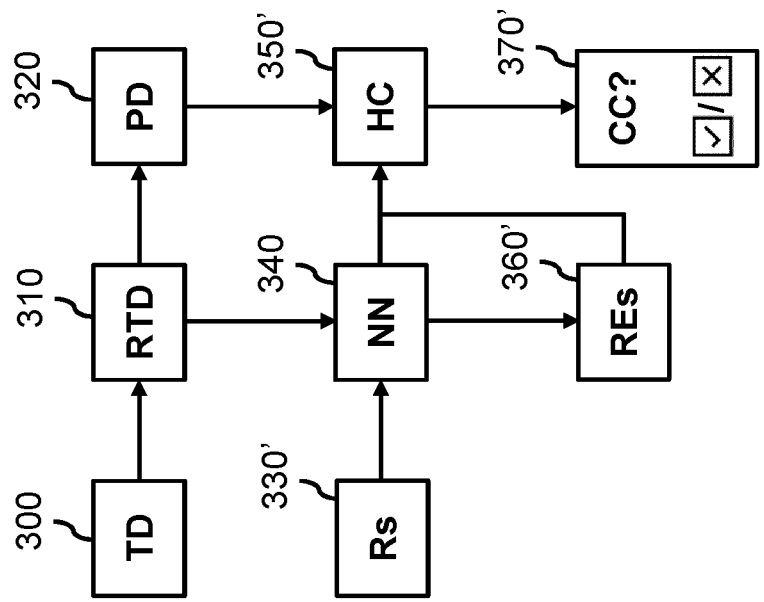
FIG. 3b shows a detailed example of how a population descriptor may be determined and used to determine conformance of multiple records, in this case, by performing a histogram comparison.

The following list of reference numbers is provided for facilitating the interpretation of the drawings and shall not be construed as limiting the claims.

| | |
|---|---|
| 020, 022 | data storage |
| 030 | training dataset |
| 040 | one or more records |
| 060 | population descriptor |
| 100 | system for processing training records |
| 120 | data interface |
| 122, 124 | data communication |
| 140 | processor subsystem |
| 200 | system for using a trained model |
| 220 | data interface |
| 222, 224 | data communication |
| 240 | processor subsystem |
| 242 | output signal |
| 260 | display output interface |
| 262 | display data |
| 280 | display |
| 282 | warning dialog box |
| 300 | training data |
| 310 | rebalanced training data |
| 320 | population descriptor (histogram) |
| 330 | record |
| 340 | trained model (neural network) |
| 350 | conformance checking |
| 360 | model output (result) |
| 370 | conformance result |
| 330' | multiple records |
| 350' | conformance checking (histogram comparison) |
| 360' | model outputs (results) |
| 370' | cohort conformance result |
| 400 | training data (images) |
| 410 | augmented training data |
| 420 | characteristic features (Shape DNA) |
| 430 | population descriptor (one-class SVM) |
| 440 | record (image) |
| 450 | trained model (Convolutional Neural Network) |
| 460 | characteristic features (Shape DNA) |
| 470 | conformance checking (one-class classification) |
| 480 | model output (segmentation) |
| 490 | conformance data (classification) |
| 500 | method of processing training records |
| 510 | accessing training dataset |
| 520 | determining characteristic features |
| 530 | determining population descriptor |
| 540 | associating population descriptor with trained model |
| 600 | method of processing at least one record |
| 610 | accessing population descriptor, record |
| 620 | determining characteristic features |
| 630 | determining conformance |
| 640 | generating output signal indicative of non-conformance |
| 700 | computer-readable medium |
| 710 | non-transitory data |

DETAILED DESCRIPTION OF EMBODIMENTS

FIG. 1 shows a system 100 for processing a trained model to determine a population descriptor associated with the trained model. The trained model may be trained on the training dataset. The trained model may be trained to provide a model output when applied to a record. The model population may be determined based on characteristic features associated with training records on which the trained model is trained.

A system 100 may comprise a data interface 120 and a processor subsystem 140 which may internally communicate via data communication 124. The processor subsystem 140 may be configured to, during operation of the system 100 and using the data interface 120, access training dataset 030 on which a trained model is trained. Optionally, the processor subsystem 140 may be configured to, during operation of the system 100 and using the data interface 120, access the trained model. The training dataset 030 may comprise a plurality of training records. For example, as shown in FIG. 1, the data interface 120 may provide access 122 to an external data storage 020 which may comprise said data 030. Alternatively, the data 030 may be accessed from an internal data storage which is part of the system 100. Alternatively, the data 030 may be received via a network from another entity. In general, the data interface 120 may take various forms, such as a network interface to a local or wide area network, e.g., the Internet, a storage interface to an internal or external data storage, etc. The data storage 020 may take any known and suitable form.

The processor subsystem 140 may be further configured to, during operation of the system 100, determine one or more characteristic features of a training record of training dataset 030. The one or more characteristic features may characterize the training record and/or a model output of applying the trained model to the training record. The processor subsystem may determine a population descriptor 060 based on the characteristic features associated with the training records. The population descriptor 060 may characterize a distribution of the one or more characteristic features over the training dataset 030. The processor subsystem 140 may further associate the population descriptor 060 with the trained model to enable an entity applying the trained model to at least one record to determine whether the at least one record conforms to the population descriptor based on determining the one or more characteristic features of the at least one record. An example of such an entity is the system 200 of FIG. 2.

The population descriptor 060 may be stored by the system 100 in the data storage 020 or elsewhere, sent via a network, etc. In general, the population descriptor 060 may be stored in a same data container as the trained model, for example in a same file(s), but may also be provided as a separate population descriptor 060 which is associated with the trained model. For example, in some embodiments, the trained model may link to the population descriptor 060, e.g., by containing an URL at which the population descriptor 060 is accessible, or the population descriptor 060 may link to the trained model. Various other means of association are equally conceivable and within reach of the skilled person.

Figure 3A:
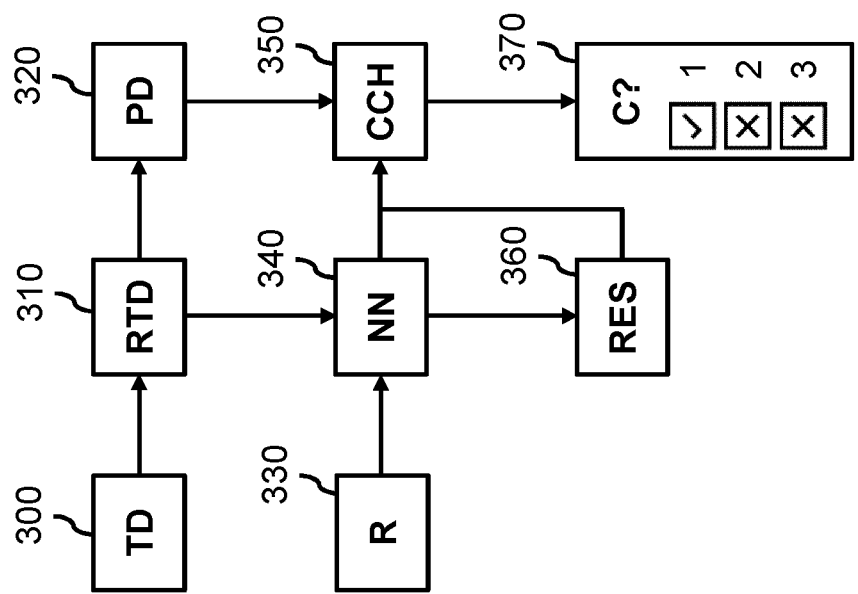
FIG. 3a shows a detailed example of how a population descriptor, in this case, probability data, may be determined for a training dataset, and used to determine conformance of a record.

Various details and aspects of the operation of the system 100 will be further elucidated with reference to FIG. 3a and others, including optional aspects thereof.

In general, the system 100 may be embodied as, or in, a single device or apparatus, such as a workstation, e.g., laptop or desktop-based, or a server. The device or apparatus may comprise one or more microprocessors which execute appropriate software. For example, the processor subsystem may be embodied by a single Central Processing Unit (CPU), but also by a combination or system of such CPUs and/or other types of processing units, such as Graphics Processing Units (GPUs). The software may have been downloaded and/or stored in a corresponding memory, e.g., a volatile memory such as RAM or a non-volatile memory such as Flash. Alternatively, the functional units of the system, e.g., the data interface and the processor subsystem, may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses, such as distributed servers, e.g., in the form of cloud computing.

FIG. 2 shows a system 200 for processing at least one record to which a trained model is to be applied and for determining whether the at least one record conforms to the population descriptor associated with the trained model. The system 200 may comprise a data interface 220 and a processor subsystem 240 which may internally communicate via data communication 224. The processor subsystem 240 may be configured to, during operation of the system 200 and using the data interface 220, access the population descriptor 060 associated with a trained model as described with reference to FIG. 1, as well as at least one record 040 to which the trained model is to be applied. Optionally, processor subsystem 240 is also configured to, during operation of the system 200 and using the data interface 220, access the trained model to which population descriptor 060 is associated. For example, as also shown in FIG. 2, the data interface 220 may provide access 222 to an external data storage 022 which comprises said data 040, 060. Alternatively, the data 040, 060 may be accessed from an internal data storage. Alternatively, the data 040, 060 may be received via a network. In general, the data interface 220 may take various forms, such as a network interface to a local or wide area network, e.g., the Internet, a storage interface to an internal or external data storage, etc. The data storage 022 may take any known and suitable form.

The processor subsystem 240 may be further configured to, during operation of the system 200, determine the one or more characteristic features of the at least one record 040, determine a deviation of the one or more characteristic features of the at least one record 040 from the distribution of said characteristic features over the training dataset to determine whether the at least one record 040 conforms to the population descriptor 060, and, if the at least one record 040 does not conform to the population descriptor of the trained model, generate an output signal 242 indicative of said non-conformance. As an optional component, the system 200 may comprise a display output interface 260 or any other type of output interface for outputting the output signal 242 to a rendering device, such as a display 280. For example, the display output interface 260 may generate display data 262 for the display 280 which causes the display 280 to render the output signal in a sensory perceptible manner, e.g., as an on-screen warning dialog box 282.

In general, the system 200 may be embodied as, or in, a single device or apparatus, such as a workstation, e.g., laptop or desktop-based, or as part of an (medical) imaging apparatus or device, or a mobile device. The device or apparatus may comprise one or more microprocessors which execute appropriate software. For example, the processor subsystem may be embodied by a single Central Processing Unit (CPU), but also by a combination or system of such CPUs and/or other types of processing units. The software may have been downloaded and/or stored in a corresponding memory, e.g., a volatile memory such as RAM or a non-volatile memory such as Flash. Alternatively, the functional units of the system, e.g., the data interface and the processor subsystem, may be implemented in the device or apparatus in the form of programmable logic, e.g., as a Field-Programmable Gate Array (FPGA). In general, each functional unit of the system may be implemented in the form of a circuit. It is noted that the system 200 may also be implemented in a distributed manner, e.g., involving different devices or apparatuses, such as the client and server of a client-server implementation.

FIG. 3a shows a detailed yet non-limiting example of how a population descriptor may be determined, for example, by the system 100 of FIG. 1, and/or used to determine conformance of a record, for example, by the system 200 of FIG. 2. For example, the techniques described here may be used for the classification of images, e.g., medical images like computed tomography (CT) scans, magnetic resonance (MR) scans, ultrasound (US) scans, or X-rays. The techniques described here may also be applied, for instance, to time series data acquired with monitoring equipment in an intensive care unit (ICU), such as blood pressure, electrocardiogram (ECG) data, respiratory rate, etcetera. For example, such images or time series data may be used for classification with respect to a number of potential diseases or pathologies, say, $b_1, \ldots, b_m$.

Training dataset TD, 300 may comprise a plurality of training records, or samples, $I_1, \ldots, I_n$. For instance, training dataset TD may comprise patient records, monitoring signals, images, image sequences, a combination of images and signals, etcetera. A training record may comprise one or more features $s_i$ descriptive of measurement parameters corresponding to the record, e.g., imaging parameters such as a type of MR imaging sequence, a presence of a contrast agent, etcetera. A training record may comprise a number of intended model outputs/annotations $B_i$ that the model is trained to approximate. For instance, such annotations may indicate the presence of distinct diseases or pathologies of the individual. A training record may also comprise one or more features $t_i$ of the subject, e.g., patient, to whom the record refers, e.g., the patient that was imaged. For example, such features may include gender, age, weight, height, smoker/non-smoker, etc. A record of training dataset TD may be represented accordingly as $s_i, t_i, I_i, B_i$.

Optionally, particular parts of the training dataset may be used more often during training or get a different weight during the training, resulting in rebalanced training dataset RTD, 310. For example, if training dataset TD has an imbalance with respect to a particular classification, then records having the less-occurring classification may be duplicated in rebalanced training dataset RTD. For example, one class of the classification may occur far less than another class in the training dataset, for instance, a class representing a rare disease. To improve recognition of this rare class, a higher weight may be assigned to it, for example, by copying records of the rare class a number of times corresponding to the weight. However, this is optional and rebalanced training dataset RTD can also be the same as training dataset TD. Similarly to above, a record of rebalanced training dataset RTD may be represented as $s_i, t_i, I_i, B_i$.

A trained model NN, 340 may be trained on the rebalanced training dataset RTD, or on the original dataset TD if no rebalancing is performed. For example, the system determining the population descriptor may train a machine learning model on the dataset itself or may obtain trained model NN from another entity. In this example, trained model NN may be a neural network trained to provide as a model output a prediction of an annotation b for a record R, 330, e.g., comprising an image I with imaging parameters s and patient parameters t, resulting in a model output RES, 360, e.g., $b = F_{NN}(I, s, t)$. For example, trained model NN may be trained using known neural network training methods, e.g., based on backsubstitution and/or stochastic gradient descent. Values s, t may be regarded as metadata associated with image I; in this example, this metadata is also input to the trained model. However, other types of trained models can be applied here as well, including models NN learned with unsupervised training.

Based on the training data RTD/TD, a population descriptor may be determined, in this case, comprising probability data PD, 320, of one or more characteristic features of the training dataset 300. A characteristic feature of a training record may be based on the training record itself. For instance, the characteristic features may comprise one or more features of the training record, e.g., imaging parameters s and/or patient parameters t. A characteristic feature may also be derived from multiple features of the training record, e.g., it may be a maximum or average of two features, etcetera. In some embodiments, the characteristic features are based on a strict subset of the features of the training records RTD/TD, e.g., at most half of the features, or at most 1, 5, or 10 features. However, it is also possible to use all features. A characteristic feature may be computed from the training record. In an embodiment, some or all of the training records RTD/TD may comprise images and a characteristic feature may be computed, e.g., extracted, from an image, e.g., as an average greyscale value, as a color spectrum, etcetera.

In some embodiments, a characteristic feature may be based on metadata, for example, metadata that is associated with training records RTD/TD but not used when training the model NN. For example, a training record may comprise an image on which model NN is trained, e.g., the model may provide an object recognition or a segmentation of the image. Such a model NN may not use metadata associated with the image, e.g. information about the imaging conditions and/or about the object being imaged, but such metadata may nonetheless be useful to characterize the training dataset.

In various embodiments, a characteristic feature may also be based on a model output of applying the trained model NN to the training record. For example, the characteristic features may comprise a classification or a regression comprised in the model output. A characteristic feature may be computed from a model output. As an example, a training record of dataset TD/RTD may comprise an image that the trained model is trained to provide a segmentation of. A characteristic feature may be computed from such a segmentation, e.g., a characteristic feature may be indicative of a dimension of an imaged object, e.g., a volume of an imaged object such as a heart. A characteristic feature of a training record for supervised learning may be based on the intended model output from training dataset TD/RTD and/or on the model output of applying trained model NN. It is not necessary to use model outputs as characteristic features. In some embodiments, the characteristic features of a record are determined without, or separate from, applying trained model NN.

For example, a rare model output used as a characteristic feature may indicate non-conformance of a record to the training dataset, especially when combined with characteristic features of the record that led to the rare model output. In case of non-supervised learning, the model output of a training record is typically obtained by applying the trained model NN to the training record. In case of supervised learning, the model output of a training record may be the desired output comprised in the training dataset TD/RTD, the actual model output of the trained model NN, or a combination of the two.

Probability data PD may enable an entity applying the trained model to determine a probability of the one or more characteristic features of a record occurring, e.g., may allow to estimate one or more probability distributions p(b, s, t), $p_s(s)$ and/or $p_t(t)$ or marginal distributions thereof related to some or all model outputs b, imaging parameters s and/or patient parameters t.

Probability data PD may be determined using known techniques such as building of histograms. Probability data PD may for instance comprise percentages in each class for binary or discrete data (with e.g. less than 100 possible values). Probability data PD may also comprise mean, median, variance or similar statistical descriptors for continuous data that follow a normal distribution. Probability data PD can also comprise a more precise probability distribution, e.g. the values of percentiles like 0 . . . 100 for a continuous parameter as e.g. age, weight, height. Probability data PD can also contain a correlation value indicative of a correlation between two characteristic features, e.g., a covariance matrix for combinations of parameters. Each of these types of probability data may refer to a model input, e.g., an imaging parameter s, a patient parameter t, a model output, or a combination.

As discussed, particular parts of the training dataset may be used more often during training or get a different weight during the training, resulting in rebalanced training dataset RTD, 310. For example, the rebalancing may comprise making several copies of specific sets of training records during training to balance data properties, e.g., duplicating records with rare classifications. Probability data PD may also be determined according to these assigned weights. For instance, probability data PD may be based on rebalanced training dataset RTD, or probability data PD may be based on training dataset TD but with the same weights applied, e.g., items may be counted in a histogram of probability data PD a number of times corresponding to their weight. For instance, this may improve the judgement of whether the model is suitable for the rare cases, e.g., without such rebalancing, non-conformance to the population descriptor may be determined because comparatively few rare cases are been in the training set.

Based on probability data PD, conformance checking CCH, 350, may be performed to determine whether record R, e.g., a record not in training dataset TD, conforms to the population descriptor. The result C?, 370, may be indicative of trustworthiness of model output RES obtained from applying trained model NN to the record R and may, for instance, be presented to a user alongside the model output. To perform conformance checking CCH, the one or more characteristic features of record R may be determined, e.g., selected, that were also used to determine probability data PD. For example, based on a distinct parameter or parameter combination, a probability of that parameter or combination occurring according to probability data PD may be determined, e.g., by obtaining the probability from a histogram of probability data PD or by evaluating a probability density function given by a statistical descriptor of probability data PD. Optionally, such a determined probability may be divided by a maximum probability, e.g., a highest frequency from the histogram, a probability density at a maximum, etc., leading to a confidence value between 0 and 1.

Result C? of conformance checking CCH may be provided via an output interface to a rendering device, for instance, the result may be presented on a screen. For example, determined conformance or non-conformance for one or more parameters or parameter combinations may be rendered. Instead or in addition, values computed to determine conformance, e.g., a determined probability, may be displayed. Shown in the figure are results of three conformance checks with respect to three sets of characteristic features: a first conformance check labeled "1", for example, based on an age feature of record R; a second conformance check labelled "2", for example, based on a Body-Mass Index (BMI) feature of record R; and a third conformance check labelled "3", for example, an overall conformance check based on features of record R as well as model output RES. Conformance is here indicated by means of a checkbox, but other indications such as color codes can be used instead or in addition. In case a non-conformance is determined, e.g., a specific value is below a threshold, an output signal indicating the non-conformance may be generated, e.g., a warning may be presented that the trained model NN is not applicable.

In a specific example, the techniques described with respect to FIG. 3a may be used in medical signal processing, for example, predictive analytics for intensive care units (ICUs). In such an application, training dataset TD may comprise annotated time series data, wherein a training record of the training data may comprise various input meta-parameters, e.g., data that, in some embodiments, is not used to train model NN. For example, the input meta-parameters may comprise patient demographic parameters, e.g., one or more of age, gender, weight, race; vital parameters, e.g., one or more of blood pressure, heart rate, respiratory rate; lab values; and/or temporal variation characteristics of the aforementioned. For example, the input dataset may comprise records of the MIMIC database of ICU encounters. Conformance checking CCH may allow to assess, detect, and/or flag for instance pediatric patient data that is erroneously fed to a model that was trained only on adults, or combinations of input parameters that were never or rarely seen in the training dataset. For example, such conformance checking could be performed when applying model NN on records R from other settings, e.g., an emergency department, where patients may be expected to exhibit a different case mix, different prevalence of conditions and/or different criticality.

In another specific example, the techniques described with respect to FIG. 3a may be used to train a model NN that allows to predict events. For example, training dataset TD may comprise vital parameters, lab values, patient demographics, interventions, and/or other parameters, e.g., the dataset may comprise records from curated training datasets such as MIMIC and/or eICU. For example, model NN may be a hemodynamic instability indicator model. In this context, the inventors found that feeding pediatric input data R to a model NN trained on adult data could result in degraded performance. Using age as a characteristic parameter of the training dataset TD in combination with the techniques described herein may allow to flag patients that do not conform to training dataset TD, e.g., whose age is e.g. below a threshold percentile in training dataset TD. For this, interestingly, it may not be necessary to know, when training model NN and/or processing the trained model to obtain probability data PD, that under-age subject data might be fed to the algorithm later. For example, the techniques described herein allow an automated determination while using trained model NN that a record R to which the model is to be applied does not conform, e.g., is out-of-scope, with respect to a particular characteristic feature, and thus possibly untrustworthy.

FIG. 3b shows another detailed yet non-limiting example of how a population descriptor may be determined, for example, by the system 100 of FIG. 1, and/or used, for example, by the system 200 of FIG. 2. In this example, system 200 determines conformance of multiple records.

The example of FIG. 3b may be based at least in part in FIG. 3a, for instance, training data TD, 300; rebalanced training data RTD, 310; population descriptor PD, 320, e.g., probability data such as a histogram; and/or trained model NN, 340, e.g., a neural network, may be as in FIG. 3a.

In this example, the trained model is applied to multiple records Rs, 330', obtaining results REs, 360'. Also, conformance checking HC, 350' is performed for the multiple records Rs, e.g., it is determined whether records Rs, e.g., as a group, conform to the probability data PD comprised in the population descriptor. In other words, performance of the trained model, in this case neural network NN, over a cohort of individuals is considered. For instance, the non-conformance determination may be used to detect model and/or concept drift, e.g., of records Rs with respect to training dataset TD.

Determining whether the multiple records Rs conform to probability data PD may comprise determining, in unit HC, 350', a probability of one or more characteristic features determined for each of the multiple records Rs occurring according to the probability data. For example, determining the conformance may comprise determining probability data, e.g., estimates of probability functions $\tilde{p}(b, s, t)$ $\tilde{p}_s(s)$ and/or $\tilde{p}_t(t)$, for training records Rs and comparing this probability data to the information PD determined for training dataset TD. For example, the probability functions may be based on model output b, imaging parameters s, and/or patient parameters t. In order to determine conformance, for example, histograms may be determined both for training dataset TD in probability data PD and for records Rs, in which case unit HC may perform a histogram consistency test to test if both histograms represent the same population, for example as described in Frank C. Porter, "Testing Consistency of Two Histograms", 2008, arXiv:0804.0380 [physics.data-an] (incorporated herein by reference). Determining conformance may also comprise, for example, performing a statistical test to compare probability data PD of the training dataset TD to records Rs encountered during use, e.g. a Wilkinson or Student test.

As in FIG. 3a, the result CC?, 370', of the conformance determination of the multiple records Rs to population descriptor PD may be output to a rendering device such as a screen, for example, only in case of non-conformance, only in case of conformance, or in both cases. For instance, conformance or non-conformance of multiple records Rs, e.g., the cohort of patients, may be rendered alongside the conformance or non-conformance of individual records of Rs, e.g., determined as described with respect to FIG. 3a, and/or alongside the determined model outputs for the records Rs. This may allow a user to make a better determination of whether to trust a model output of trained model NN on a given record by taking into account both whether its cohort generally conforms to the training dataset TD of trained model NN, and hence, whether the trained model may be generally expected to provide trustworthy model outputs in the setting of the given record, and whether the given record itself conforms to the training dataset TD, and hence, whether the model is expected to provide a trustworthy model output on the given record.

The processor subsystem of the system using trained model NN may be further configured to adapt a model parameter of trained model NN in response to the output signal indicating non-conformance. For example, a classification threshold may be adapted, e.g., to balance between precision and recall. In an embodiment, non-conformance is indicative of increased prevalence of a disease, for instance, non-conformance may be based on determining that a disease diagnosis output by trained model NN occurs more often in records Rs than in training dataset TD. In such cases, model parameters of trained model NN may for instance be adjusted to increase sensitivity, e.g., recall.

As a particular example, trained model NN may be trained to diagnose a disease on an input image, e.g., trained model NN may be trained to detect presence/absence of tuberculosis based on the image. The inventors were able to build an accurate trained model NN for this task based on a training dataset TD from a working-age screening population coming into one particular country. When this trained model NN is applied in a different context, however, e.g. frail elderly in another geography, accuracy of the model may decrease. In such cases, conformance checking CCH of FIG. 3a may for instance allow to automatically assess and flag outliers, e.g., in terms of age, gender, race, BMI, or a combination thereof. For this, no explicit/manual coding that trained model NN applies only to particular geography may be necessary, and moreover, the trained model may not be needlessly limited to a such a manually coded training cohort and geography. As a consequence, trained model NN may be used on a wider range of subjects. Moreover, in case of a higher prevalence of a model output than during training, e.g., a tuberculosis diagnosis, model parameters may be adapted to account for the new situation. For instance, the higher prevalence may indicate a regional outbreak of tuberculosis. As a possible reaction, sensitivity of the model may be temporarily increased at the expense of specificity.

More generally, conformance checking HC may allow to compare distributions of inputs and/or outputs from the execution setting of trained model NN to the distribution in the training dataset TD. For instance, records Rs compared to the training dataset may comprise a moving average of data over the last month. Based on probability data over the training dataset TD, e.g., median and temporal variance references for the positivity rate, conformance checking HC may flag whenever the actual positivity rate in the execution phase deviates significantly. For instance, in such cases, an output signal, e.g., a model drift alert, may be generated and possibly output to a user, e.g., a clinical user or a data science expert.

Figure 4:
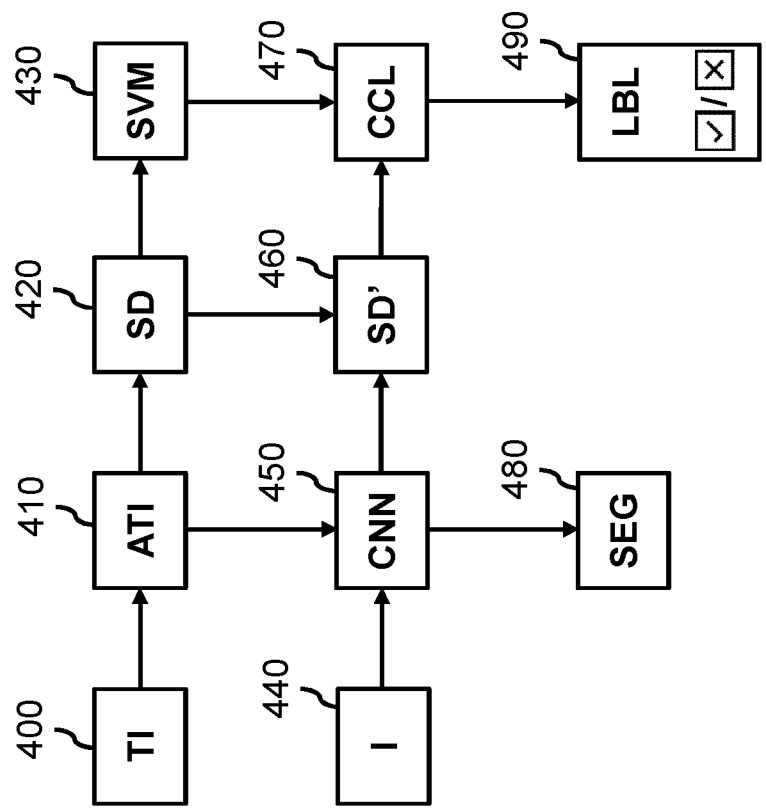
FIG. 4 shows a detailed example of how a population descriptor, in this case, Shape DNA of segmentations of training images, may be determined and used to determine conformance of a model output on a record, in this case, a segmentation of an image.

FIG. 4 shows another detailed yet non-limiting example of how a population descriptor may be determined, for example, by the system 100 of FIG. 1, and/or used to determine conformance of a record, for example, by the system 200 of FIG. 2.

In the example shown in FIG. 4, training dataset TI, 400, may comprise a plurality of images $I_i$, for example, with corresponding annotations $B_i$. For example, an annotation of an image may comprise a segmentation of the image, e.g., a segmentation of an organ in the image. Optionally, before training a model on training dataset TI, first, an augmented training dataset ATI, 410, is derived from training dataset TI. For example, known data augmentation techniques may be used to transform images $I_i$ and/or annotations $B_i$, resulting in an augmented training dataset ATI comprising an increased number of images, for example, with corresponding annotations. For example, non-linear transformations may be used, for example, non-linear transformations generated by non-rigid registration of two images of training dataset TD and application of the transformation to remaining images in training dataset TD. For example, the non-linear transformations may be used as disclosed in Tom Vercauteren et al.; "Non-parametric Diffeomorphic Image Registration with the Demons Algorithm"; Proceedings of MICCAI 2007; Springer LNCS vol 4792 (incorporated herein by reference).

Training dataset TI, or, if augmentation is used, augmented training dataset ATI, may be used to train a model CNN, 450, in this example, a Convolutional Neural Network (CNN). For example, the training images with their corresponding annotations may be used in training, for example, to train an F-net as disclosed in Tom Brosch, Axel Saalbach; "Foveal fully convolutional nets for multi-organ segmentation"; Proceedings Volume 10574, Medical Imaging 2018: Image Processing; 105740U; 2018 (incorporated herein by reference). Trained model CNN may be a voxel classifier. For instance, trained model CNN may be trained to provide, upon input of a record comprising an image, a segmentation of that image. Apart from neural networks, various other types of trained models may be used, e.g., the trained model may be a model-based segmentation model, e.g., as disclosed in Olivier Ecabert et al.; "Segmentation of the heart and great vessels in CT images using a model-based adaptation framework"; Medical Image Analysis; 15(6); 2011 (incorporated herein by reference).

Based on training dataset TI, or, if augmentation is used, augmented training dataset ATI, characteristic features of training records of the dataset may be determined. In the present example, the characteristic features of a training image $I_i$ comprise one or more shape descriptors SD, 420, of the shape represented in image $I_i$ and/or segmentation B. For example, the shape descriptors may comprise one or more ShapeDNA features. ShapeDNA features may be particularly useful in settings where scale invariance and/or performance for shape retrieval of non-rigid shapes are important. Determining the characteristic features may comprise analyzing geometric properties of segmentation B. For example, spectral shape analysis may be used to determine the characteristic features. Spectral shape analysis techniques are known, for instance, from Marc Niethammer et al.; "Global Medical Shape Analysis Using the Laplace-Beltrami Spectrum"; Proceedings MICCAI 2007, Springer LNCS vol 4791 (incorporated herein by reference). For instance, such analysis may use the spectrum, e.g., eigenvalues and/or eigenfunctions of the Laplace-Beltrami operator to derive various shape descriptors, e.g., ShapeDNA.

Instead of or in addition to features derived by spectral shape analysis, shape descriptors SD may comprise transformation parameters and/or shape eigenmodes, for example, in combination with model-based segmentation. Shape descriptors SD may also be otherwise derived from a segmentation $B_i$, e.g., the shape descriptors may comprise a dimension, a volume, etcetera of an object, e.g., organ, identified in the image. Manually defined limits may be applied to such shape descriptors, e.g., e.g. a minimum/maximum size of an organ.

Determining shape descriptors SD may also comprise assessing an orientation of a shape with respect to the coordinate system of the image, for instance, using Euler angles for the eigenvectors of the moment of inertia tensor, or using a matrix of cosines. This may be especially useful for non-spherical segmentation results, e.g., prolate or oblong tumors. Shape descriptors SD may optionally include a location of an object, e.g., a center of gravity, e.g., with respect to the image coordinate system or with respect to other objects or structures in the image.

Shape descriptors SD may also be combined with additional characteristic features, e.g., characteristics based on metadata associated with images TI. For instance, metadata such as details s of the imaging protocol and/or parameters t of the imaging subject may be included, as described with respect to FIG. 3a. For example, the characteristic features may comprise a focal length, e.g., allowing to detect non-conformance when a model trained on normal/tele-lens photos is applied to an image taken with a fish-eye lens. For medical imaging processing applications, similarly, a source detector distance (SDD) may be used as a characteristic parameter. Interestingly, in some embodiments, such metadata may not be input to trained model CNN but still be used to determine conformance.

Moreover, some characteristic features may be derived from the images themselves, e.g., an average and/or median grey value of an image, a noise measure, etcetera. For instance, such derived features may be useful in medical image processing, e.g. in an automated organ segmentation setting to flag input images with a worse signal-to-noise ratio than images in the training dataset or an unexpected MRI contrast that was not seen in training. Moreover, the use of various metadata or derived features may be used to detecting manipulation/tampering or fraud, e.g., images that have been manipulated to force a particular output of the trained model.

The characteristic features, including shape descriptors SD, may be used to determine a population descriptor, in this example, a one-class classifier SVM, 430 such as a one-class Support Vector Machine (SVM). One-class classifier SVM may enable to classify a record as being conformant when using the model. For instance, the classifier may verify whether a segmentation result is within the range of expectations, e.g., regarding shape properties. For example, the outlier detection approach may be used disclosed in Axel Saalbach et al.; "Failure Analysis for Model-Based Organ Segmentation Using Outlier Detection"; Proceedings Volume 9034, Medical Imaging 2014: Image Processing; 903408; 2014 (incorporated herein by reference).

In the system for using trained model CNN, the model CNN may be applied to a new image I, 440, resulting in a mode output, e.g., segmentation, SEG, 480. Analogously to above, characteristic features SD', 460, of the annotation, e.g., shape descriptors of segmentation SEG, may be determined, for example, using spectral shape analysis. In conformance checking CCL, 470, One-class classifier SVM may be used to determine label LBL, 490, classifying annotation SEG as normal, e.g., conforming to training dataset TI, or as an outlier.

In various embodiments, segmentations of images TI, I may comprise multiple connected components. In such cases, determining shape descriptors SD may comprise executing a connected component analysis as known per se on a segmentation of an image TI, I. In some embodiments, one of the connected components may be selected, e.g., the largest object, and shape descriptors SD may be determined of that selected connected component. For example, this may be particularly useful when a voxel classifier is used that may provide detection results disconnected from the main object. In other embodiments, e.g., where segmentation may be expected to result in several objects such as vertebrae, shape descriptors SD may be determined and/or conformance determination may be performed for several, e.g., all, identified connected components.

Figure 5:
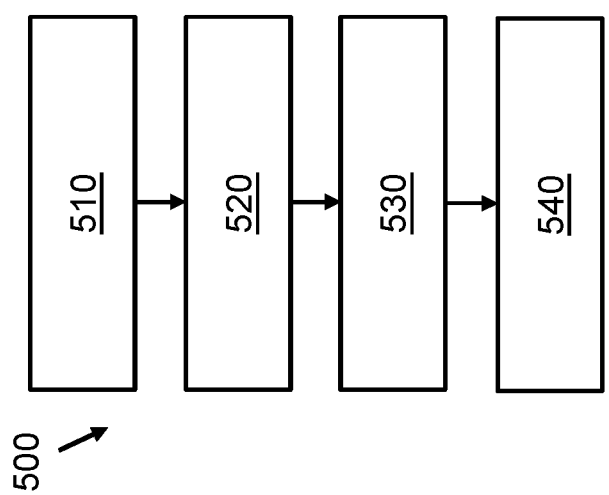
FIG. 5 shows a computer-implemented method of processing training records of a training dataset to determine a population descriptor that characterizes a distribution of one or more characteristic features over the training dataset.

FIG. 5 shows a block-diagram of computer-implemented method 500 of processing training records of a training dataset. The method 500 may correspond to an operation of the system 100 of FIG. 1. However, this is not a limitation, in that the method 500 may also be performed using another system, apparatus, or device.

The method 500 may comprise, in an operation titled "ACCESSING TRAINING DATASET", accessing 510 a training dataset for a trained model, the training dataset comprising a plurality of training records, wherein the trained model is trained on the training dataset to provide a model output when applied to a record. The method 500 may further comprise, in an operation titled "DETERMINING CHARACTERISTIC FEATURES", determining 520 one or more characteristic features for a training record of the training dataset, said one or more characteristic features characterizing the training record and/or a model output provided when the trained model is applied to the training record. The method 500 may further comprise, in an operation titled "DETERMINING POPULATION DESCRIPTOR", determining 530 a population descriptor characterizing a distribution of the one or more characteristic features over the training dataset. The method 500 may further comprise, in an operation titled "ASSOCIATING POPULATION DESCRIPTOR WITH TRAINED MODEL", associating the population descriptor with the trained model to enable an entity which applies the trained model to at least one record to determine whether the at least one record conforms to the population descriptor by determining the one or more characteristic features for the at least one record and by determining a deviation of said one or more characteristic features from the distribution of said characteristic features over the training dataset.

Figure 6:
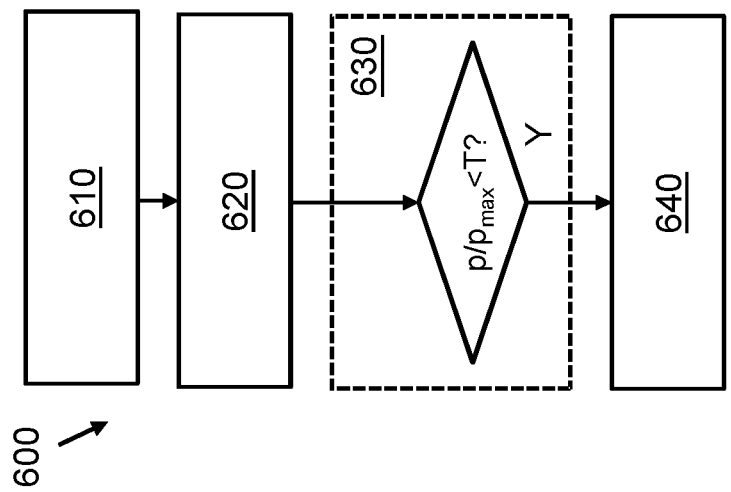
FIG. 6 shows a computer-implemented method of processing at least one record on which a trained model is to be applied and determining whether the at least one record conforms to the population descriptor.

FIG. 6 shows a block-diagram of computer-implemented method 600 for using a trained model. The method 600 may correspond to an operation of the system 200 of FIG. 2. However, this is not a limitation, in that the method 600 may also be performed using another system, apparatus, or device.

The method 600 may comprise, in an operation titled "ACCESSING POPULATION DESCRIPTOR, RECORD", accessing 610 a population descriptor associated with the trained model, the trained model having been trained on a training dataset, the training dataset comprising a plurality of training records, the population descriptor characterizing a distribution of one or more characteristic features for the training records over the training dataset, the one or more characteristic features of a training record characterizing the training record and/or a model output provided when applying the trained model to the training record; and the at least one record to which the trained model is to be applied. The method 600 may further comprise, in an operation titled "DETERMINING CHARACTERISTIC FEATURES", determining 620 the one or more characteristic features of the at least one record. The method 600 may further comprise, in an operation titled "DETERMINING CONFORMANCE", determining 630 whether the at least one record conforms to the population descriptor by determining a likelihood of the one or more characteristic features of the at least one record occurring according to their distribution over the training dataset. For example, such determining may involve determining a probability $p/p_{max}$ of the determined characteristic features occurring according to probability data comprised in the population descriptor and comparing the determined probability to a threshold T. The method 600 may further comprise, in an operation titled "GENERATING OUTPUT SIGNAL INDICATIVE OF NON-CONFORMANCE", if the at least one record does not conform to the population descriptor of the trained model, generating 640 an output signal indicative of said non-conformance.

It will be appreciated that, in general, the operations of method 500 of FIG. 5 and/or method 600 of FIG. 6 may be performed in any suitable order, e.g., consecutively, simultaneously, or a combination thereof, subject to, where applicable, a particular order being necessitated, e.g., by input/output relations.

Figure 7:
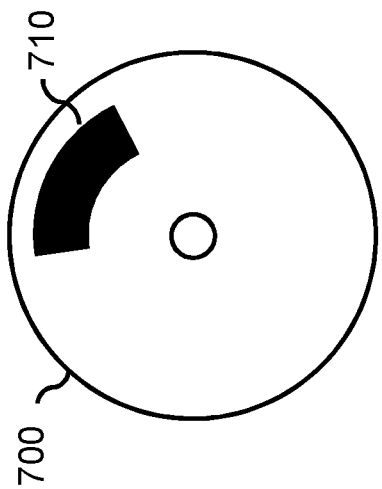
FIG. 7 shows a computer-readable medium comprising data.

The method(s) may be implemented on a computer as a computer implemented method, as dedicated hardware, or as a combination of both. As also illustrated in FIG. 7, instructions for the computer, e.g., executable code, may be stored on a computer readable medium 700, e.g., in the form of a series 710 of machine-readable physical marks and/or as a series of elements having different electrical, e.g., magnetic, or optical properties or values. The executable code may be stored in a transitory or non-transitory manner. Medium 700 may, instead or in addition, store data representing a trained model and a population descriptor associated with the trained model, the trained model having been trained on a training dataset, the training dataset comprising a plurality of training records, the population descriptor characterizing a distribution of one or more characteristic features for the training records over the training dataset, the one or more characteristic features of a training record characterizing the training record and/or a model output provided when applying the trained model to the training record. Examples of computer readable mediums include memory devices, optical storage devices, integrated circuits, servers, online software, etc. FIG. 7 shows an optical disc 700.

The following numbered clauses include embodiments that are contemplated and nonlimiting:

1. A system for processing training records of a training dataset, comprising:
   a data interface for accessing:
      a training dataset for a trained model, the training dataset comprising a plurality of training records, wherein the trained model is trained on the training dataset to provide a model output when applied to a record;
   a processor subsystem configured to:
      determine one or more characteristic features for a training record of the training dataset, said one or more characteristic features characterizing the training record and/or a model output provided when the trained model is applied to the training record;
      determine a population descriptor characterizing a distribution of the one or more characteristic features over the training dataset;
      associate the population descriptor with the trained model to enable an entity which applies the trained model to at least one record to determine whether the at least one record conforms to the population descriptor by determining the one or more characteristic features for the at least one record and by determining a deviation of said one or more characteristic features from the distribution of said characteristic features over the training dataset.

2. A system as in the preceding clause, wherein the processor subsystem is configured to train a machine learning model on the training dataset, thereby obtaining the trained model.

3. A system for processing at least one record to which a trained model is to be applied, comprising:
  a data interface for accessing:
    a population descriptor associated with the trained model, the trained model having been trained on a training dataset, the training dataset comprising a plurality of training records, the population descriptor characterizing a distribution of one or more characteristic features for the training records over the training dataset, the one or more characteristic features of a training record characterizing the training record and/or a model output provided when applying the trained model to the training record;
    the at least one record to which the trained model is to be applied;
  a processor subsystem configured to:
    determine the one or more characteristic features of the at least one record;
    determine a deviation of the one or more characteristic features of the at least one record from the distribution of said characteristic features over the training dataset to determine whether the at least one record conforms to the population descriptor;
    if the at least one record does not conform to the population descriptor of the trained model, generate an output signal indicative of said non-conformance.

4. A computer-implemented method of processing training records of a training dataset, comprising:
  accessing:
    a training dataset for a trained model, the training dataset comprising a plurality of training records, wherein the trained model is trained on the training dataset to provide a model output when applied to a record;
  determining one or more characteristic features for a training record of the training dataset, said one or more characteristic features characterizing the training record and/or a model output provided when the trained model is applied to the training record;
  determining a population descriptor characterizing a distribution of the one or more characteristic features over the training dataset;
  associating the population descriptor with the trained model to enable an entity which applies the trained model to at least one record to determine whether the at least one record conforms to the population descriptor by determining the one or more characteristic features for the at least one record and by determining a deviation of said one or more characteristic features from the distribution of said characteristic features over the training dataset.

5. A computer-implemented method of processing at least one record to which a trained model is to be applied, comprising:
  accessing:
    a population descriptor associated with the trained model, the trained model having been trained on a training dataset, the training dataset comprising a plurality of training records, the population descriptor characterizing a distribution of one or more characteristic features for the training records over the training dataset, the one or more characteristic features of a training record characterizing the training record and/or a model output provided when applying the trained model to the training record;
    the at least one record to which the trained model is to be applied;
  determining the one or more characteristic features of the at least one record;
  determining whether the at least one record conforms to the population descriptor by determining a likelihood of the one or more characteristic features of the at least one record occurring according to their distribution over the training dataset;
  if the at least one record does not conform to the population descriptor of the trained model, generating an output signal indicative of said non-conformance.

6. A computer-readable medium comprising transitory or non-transitory data representing a trained model and a population descriptor associated with the trained model, the trained model having been trained on a training dataset, the training dataset comprising a plurality of training records, the population descriptor characterizing a distribution of one or more characteristic features for the training records over the training dataset, the one or more characteristic features of a training record characterizing the training record and/or a model output provided when applying the trained model to the training record.

Examples, embodiments or optional features, whether indicated as non-limiting or not, are not to be understood as limiting the invention as claimed.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. Expressions such as "at least one of" when preceding a list or group of elements represent a selection of all or of any subset of elements from the list or group. For example, the expression, "at least one of A, B, and C" should be understood as including only A, only B, only C, both A and B, both A and C, both B and C, or all of A, B, and C. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:
1. A system for processing training records of a training dataset, comprising:
  a data interface for accessing:
    a training dataset for a trained model, the training dataset comprising a plurality of training records, wherein the trained model is trained on the training dataset to provide a model output when applied to a record;
  a processor subsystem configured to:
    determine one or more characteristic features for a training record of the training dataset, said one or more characteristic features characterizing the training record, said characteristic features being based on the training record and/or metadata associated with the training record;
    determine a population descriptor characterizing a distribution of the one or more characteristic fea- tures over the training dataset, wherein said determining does not access intermediate outputs of the trained model;

associate the population descriptor with the trained model to enable an entity which applies the trained model to at least one record to determine whether the at least one record conforms to the population descriptor by determining the one or more characteristic features for the at least one record and by determining a deviation of said one or more characteristic features from the distribution of said characteristic features over the training dataset.

2. A system as in claim 1, wherein the population descriptor comprises probability data indicative of a probability distribution of the one or more characteristic features over the training dataset.

3. A system as in claim 1, wherein the population descriptor comprises a one-class classifier trained on the one or more of characteristic features of the training records to enable the entity applying the trained model to classify the at least one record as being conformant.

4. A system as in claim 1, wherein a training record comprises an image, the processor subsystem being further configured to determine the one or more characteristic features of the training record by extracting a characteristic feature from the image and/or by determining a characteristic feature from metadata associated with the image.

5. A system as in claim 1, wherein a training record comprises an image and the trained model is trained to provide a segmentation of the image, the processor subsystem being further configured to determine a characteristic feature of the training record by extracting a shape descriptor of the segmentation of the image.

6. A system as in claim 1, wherein the characteristic features for the training record are features of the training record that were used as input when training the trained model, or metadata that was not used as input when training the trained model.

7. A system for processing at least one record to which a trained model is to be applied, comprising:
a data interface for accessing:
a population descriptor associated with the trained model, the trained model having been trained on a training dataset, the training dataset comprising a plurality of training records, the population descriptor characterizing a distribution of one or more characteristic features for the training records over the training dataset, the one or more characteristic features of a training record characterizing the training record, the one or more characteristic features being determined based on the at least one record and/or metadata associated with the at least one record, the population descriptor having been determined based on the characteristic features without accessing intermediate outputs of the trained model;
the at least one record to which the trained model is to be applied;
a processor subsystem configured to:
determine the one or more characteristic features of the at least one record;
determine a deviation of the one or more characteristic features of the at least one record from the distribution of said characteristic features over the training dataset to determine whether the at least one record conforms to the population descriptor;
when the at least one record does not conform to the population descriptor of the trained model, generate an output signal indicative of said non-conformance.

8. A system as in claim 7, further comprising an output interface for outputting the output signal to a rendering device for rendering the output signal in a sensory perceptible manner to a user.

9. A system as in claim 8, wherein the output interface is further configured to output a deviation of one or more determined characteristic features that resulted in the non-conformance to the population descriptor.

10. A system as in claim 7, wherein the data interface is configured to access population descriptors associated with multiple trained models, the processor subsystem being configured to:
determine whether the at least one record conforms to a population descriptor associated with a respective trained model; and
in case of conformance, select the respective trained model of the multiple trained models for being applied to the at least one record.

11. A system as in claim 7, wherein the processor subsystem is further configured to adapt a model parameter of the trained model in response to the output signal.

12. A computer-implemented method of processing training records of a training dataset, comprising:
accessing:
a training dataset for a trained model, the training dataset comprising a plurality of training records, wherein the trained model is trained on the training dataset to provide a model output when applied to a record;
determining one or more characteristic features for a training record of the training dataset, said one or more characteristic features characterizing the training record, said characteristic features being determined based on the training record and/or metadata associated with the training record;
determining a population descriptor characterizing a distribution of the one or more characteristic features over the training dataset, wherein said determining does not access intermediate outputs of the trained model;
associating the population descriptor with the trained model to enable an entity which applies the trained model to at least one record to determine whether the at least one record conforms to the population descriptor by determining the one or more characteristic features for the at least one record and by determining a deviation of said one or more characteristic features from the distribution of said characteristic features over the training dataset.

13. A computer-implemented method of processing at least one record to which a trained model is to be applied, comprising:
accessing:
a population descriptor associated with the trained model, the trained model having been trained on a training dataset, the training dataset comprising a plurality of training records, the population descriptor characterizing a distribution of one or more characteristic features for the training records over the training dataset, the one or more characteristic features of a training record characterizing the training record, the one or more characteristic features being determined based on the at least one record and/or metadata associated with the at least one record, the population descriptor having been determined based on the characteristic features without accessing intermediate outputs of the trained model;

the at least one record to which the trained model is to be applied;

determining the one or more characteristic features of the at least one record;

determining whether the at least one record conforms to the population descriptor by determining a likelihood of the one or more characteristic features of the at least one record occurring according to their distribution over the training dataset;

when the at least one record does not conform to the population descriptor of the trained model, generating an output signal indicative of said non-conformance.

14. A non-transitory computer-readable medium comprising transitory or non-transitory data representing instructions arranged to cause a processor system to perform the computer-implemented method according to claim 12.

15. A non-transitory computer-readable medium comprising transitory or non-transitory data representing a trained model and a population descriptor associated with the trained model, the trained model having been trained on a training dataset, the training dataset comprising a plurality of training records, the population descriptor characterizing a distribution of one or more characteristic features for the training records over the training dataset, the one or more characteristic features of a training record characterizing the training record, the one or more characteristic features being determined based on the at least one record and/or metadata associated with the at least one record, the population descriptor having been determined based on the characteristic features without accessing intermediate outputs of the trained model.

16. The computer-implemented method of claim 13, wherein the population descriptor comprises probability data indicative of a probability distribution of the one or more characteristic features over the training dataset.

17. The computer-implemented method of claim 13, wherein the population descriptor comprises a one-class classifier trained on the one or more of characteristic features of the training records to enable the entity applying the trained model to classify the at least one record as being conformant.

18. The computer-implemented method of claim 13, wherein a training record comprises an image, further comprising determining the one or more characteristic features of the training record by extracting a characteristic feature from the image and/or by determining a characteristic feature from metadata associated with the image.

19. The computer-implemented method of claim 13, wherein a training record comprises an image and the trained model is trained to provide a segmentation of the image, further comprising determining a characteristic feature of the training record by extracting a shape descriptor of the segmentation of the image.

20. The computer-implemented method of claim 13, wherein the characteristic features for the training record are features of the training record that were used as input when training the trained model, or metadata that was not used as input when training the trained model.

* * * * *